US 6,540,705 B2

(12) United States Patent
Norstrem et al.

(10) Patent No.: US 6,540,705 B2
(45) Date of Patent: Apr. 1, 2003

(54) ANKLE BRACE PROVIDING UPPER AND LOWER ANKLE ADJUSTMENT

(75) Inventors: Paul R. Norstrem, Dresser, WI (US); Cheryl L. Mattson, New Auburn, WI (US)

(73) Assignee: Core Products International, Inc., Osceola, WI (US)

( * ) Notice: Subject to any disclaimer, the term of this patent is extended or adjusted under 35 U.S.C. 154(b) by 0 days.

(21) Appl. No.: 09/791,115

(22) Filed: Feb. 22, 2001

(65) Prior Publication Data

US 2002/0115951 A1 Aug. 22, 2002

(51) Int. Cl.[7] .................................................. A61F 5/00
(52) U.S. Cl. ................................. 602/5; 602/23; 602/27
(58) Field of Search .............................. 128/845, 846, 128/869, 882; 602/5, 16, 23, 27

(56) References Cited

U.S. PATENT DOCUMENTS

| 4,280,488 A | | 7/1981 | Polsky et al. ................. 128/80 |
|---|---|---|---|
| 4,323,058 A | * | 4/1982 | Detty ........................... 602/27 |
| 4,513,740 A | | 4/1985 | Westlake ...................... 128/165 |
| 4,527,556 A | | 7/1985 | Nelson ......................... 128/80 |
| 4,651,726 A | | 3/1987 | Holland ........................ 128/166 |
| 4,878,505 A | | 11/1989 | Thanner ....................... 128/882 |
| 5,067,486 A | | 11/1991 | Hely ............................ 128/80 |
| 5,657,767 A | | 8/1997 | Nelson et al. ................. 128/882 |
| 5,795,316 A | * | 8/1998 | Gaylord ........................ 602/65 |
| 5,814,002 A | | 9/1998 | Nelson ......................... 602/27 |
| 6,024,712 A | * | 2/2000 | Iglesias ........................ 602/27 |

* cited by examiner

Primary Examiner—Michael A. Brown
(74) Attorney, Agent, or Firm—Nawrocki, Rooney & Sivertson, P.A.

(57) ABSTRACT

An ankle brace having an upper portion and a lower portion. The upper portion defines an interior having a first circumference. The lower portion defines an interior having a second circumference. The ankle brace further comprises a means for adjusting the sizes of the first and second circumferences independently from each other.

22 Claims, 3 Drawing Sheets

ANKLE BRACE PROVIDING UPPER AND LOWER ANKLE ADJUSTMENT

BACKGROUND OF THE INVENTION

This invention relates generally to the field of ankle braces and more particularly to an ankle brace for independent adjustment of the upper and the lower portions of the brace.

Ankle braces are generally employed to immobilize or inhibit the movement of the foot and ankle with respect to the leg. In this manner, an ankle injury can be healed more effectively. Ankle braces can also be employed to provide support to the joint during continuous or high stress activities. The devices have been utilized in many fields including many commercial and industrial applications.

Initially, ankle immobilization (or the inhibition of movement of the ankle) was achieved through the application of tape. However, taping takes expertise and is generally time consuming. Further, taping works well for immobilization but does not allow the joint to flex to any great degree and can also be somewhat difficult to remove.

Ankle brace devices have been devised to overcome these shortcomings. Generally, prior art ankle braces have been formed as a boot-shaped body having an open front and a hole at the heel. An opening at the toe allows the toes to move freely. The devices have generally had a tongue fitted into the open front and securing systems for holding the front edges together.

The most common securing system has provided a plurality of eyelets positioned along the front edges and a lace threaded through the eyelets and tied together at its ends to hold the front edges together. The lace can be tightened or loosened to adjust the overall size of the brace, thereby adjusting the size of the boot and/or the amount of immobilization provided.

It may be desirable to have the upper portion of the boot tightened to a different degree than the lower portion of the boot, or vice versa. These configurations cannot be achieved by the prior art devices because there is only a single lace for adjustment. Furthermore, it is sometimes desirable to make gross adjustments to the brace, for example, to test general fit, and then make fine adjustments without altering the initial gross adjustments. The lace devices of the prior art cannot accomplish this function because the lace provides only one means for both gross and fine adjustments. Additionally, the use of a single lace design provides uniform force to all areas of the front of the brace. It may be desirable in some applications to have reduced force in the region directly above the ankle. This reduced force allows the ankle some freedom of movement. The single lace design of the prior art cannot provide the increased freedom of movement necessary for such applications.

SUMMARY OF THE INVENTION

The present invention generally provides an ankle brace having an upper portion and a lower portion. The upper portion defines an interior having a first circumference. The lower portion defines an interior having a second circumference. The ankle brace further comprises a system for adjusting the sizes of the first and second circumferences independently of each other.

A preferred embodiment of the present invention generally provides a body having upper and lower portions and an open front. The brace is adapted to receive one or more laces that are arranged to span the open front and to be received by the body.

The size adjustment of the first and second circumferences may be accomplished via a plurality of tabs each having a lace receiving eyelet, the tabs being releasably and adjustably attached to the body. The tabs may be constructed and arranged to provide independent gross adjustment and/or fine adjustment of the sizes of the first and second circumferences.

Gross adjustment may be provided by two or more first tabs each having one or more eyelets for receiving a lace, one of the first tabs being releasably attached to the upper portion of the brace while another first tab is releasably attached to lower portion. Fine adjustment may be provided by two or more second tabs each having an eyelet for receiving a lace, one of the second tabs being releasably attached to the upper portion of the brace while another second tab is releasably attached to the lower portion.

In the described embodiment, the tabs are utilized in sets of one first tab and one second tab. The brace may be arranged to utilize the sets of tabs wherein one of the tabs is capable of being releasably attached to the body on one side of the front opening, while the other tab is capable of being releasably attached to the body on the other side of the front opening.

The mechanism for adjustment of the size of the upper portion of the brace may be provided by a pair of tabs each having an eyelet thereon for receiving a lace and means for releasable attachment of each tab to the body. One of the tabs is capable of being releasably attached to the body on one side of the front opening, while the other tab is capable of being releasably attached to the body on the other side of the front opening. This embodiment of the brace may be arranged such that one tab is utilized for gross adjustment and one tab for fine adjustment of the portion of the brace to which the pair is releasably attached.

The aforementioned benefits and other benefits including specific features of the invention will become clear from the following description by reference to the accompanying drawings.

DETAILED DESCRIPTION OF THE INVENTION

Figure 1:
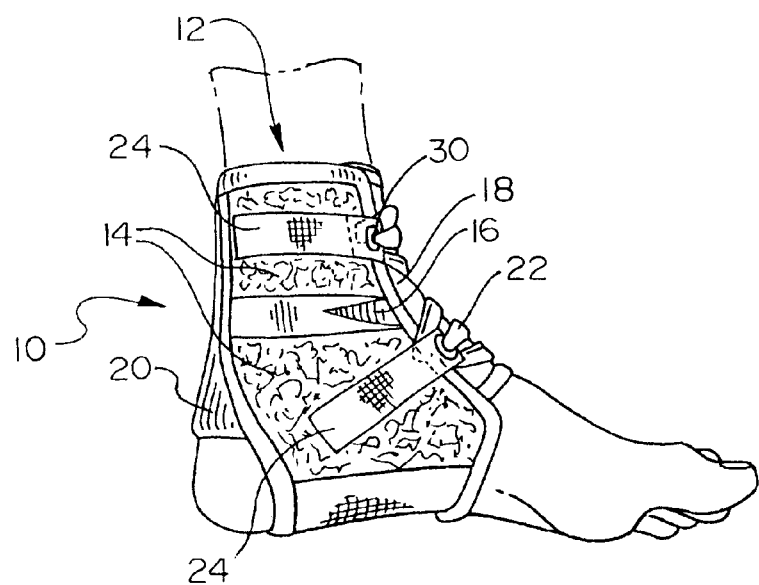
FIG. 1 is a side view of one side of an embodiment of the present invention.

Referring now to the drawings wherein like reference numerals denote like elements throughout the several views, FIG. 1 illustrates a side view of an embodiment of the present invention.

The embodiment shown in FIGS. 1–4 is generally comprised of a body 10, a plurality of tabs 24 and 28, and a lace 22. The body 10 has an opening at its front wherein a tongue 18 is positioned. Preferably, the tongue 18 is attached to the inside of the body 10 near the front edges of at least one of the side portions 12.

The main portions of the body 10 may be formed from a single piece of material that is bent into a U-shape to form the side portions 12 and a U-shaped bottom. Alternatively, the body 10 may be comprised of two or more pieces of material that are joined together.

The back edges of the side portions 12 are also to be joined together to form the back of the body 10. The joinder of the side portions at the bottom and back edges may be accomplished by any means known in the art.

Figure 4:
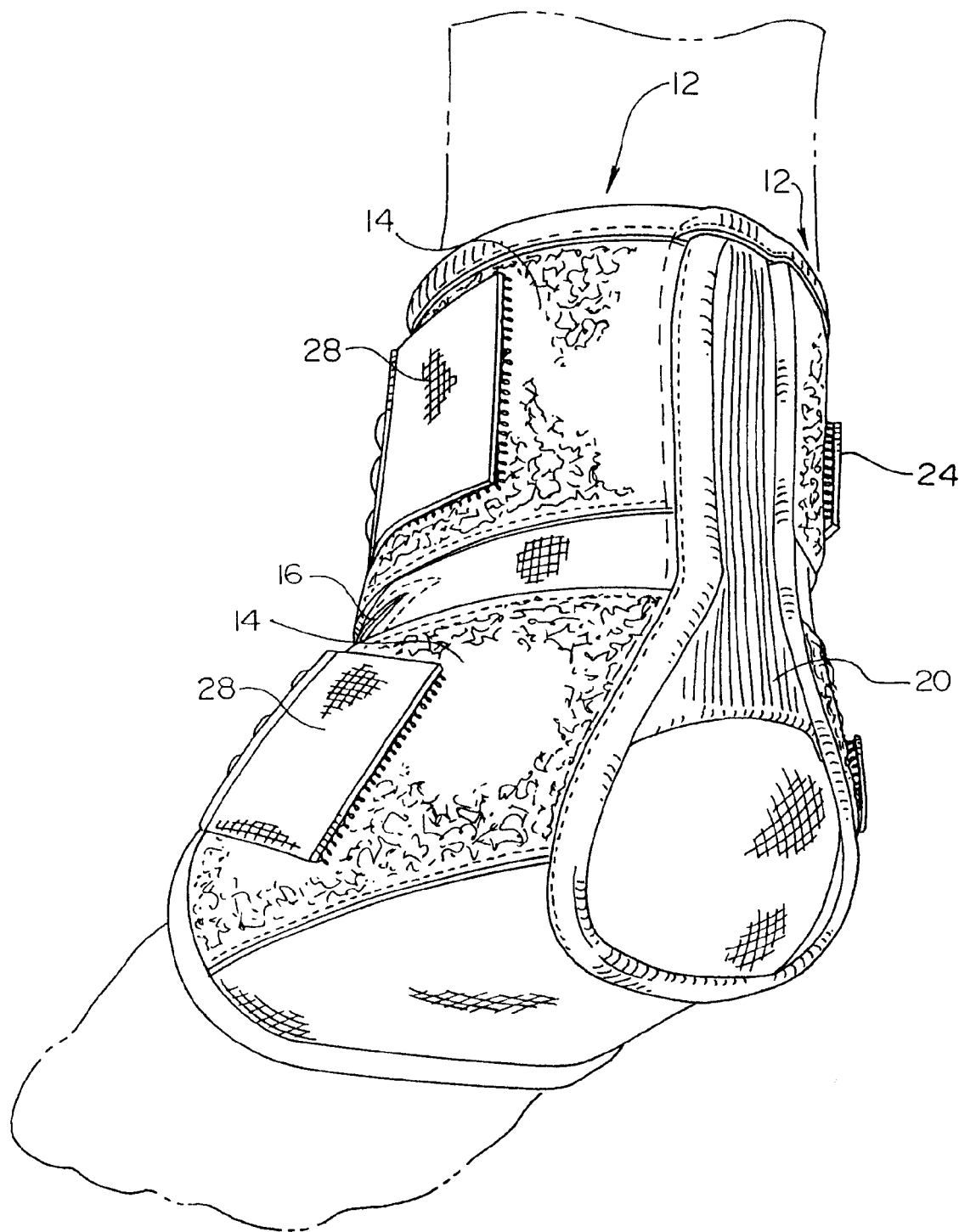
FIG. 4 is a back view of the embodiment of FIG. 1.

For example, as shown in FIGS. 1 and 4, the side portions 12 may be joined by a piece of material 20 spanning between their edges. The piece of material 20 is preferably flexible in one, or more preferably, multiple directions to enable the greatest freedom of movement to the wearer. Such material is commonly known in the art, however, has not be utilized for this specific purpose.

The body 10 may also utilize features to allow for greater flexibility of the brace, thereby, providing greater comfort to the wearer. For example, a notch 16 can be cut in the body material 10. This notch 16 allows for the movement of the ankle without having to deform the front edges of the body 10. The notch 16 may be filled with a flexible fabric material if desired.

Each side portion 12 has at least two tab attachment structures 14 affixed thereon. Any suitable structure may be utilized. For example, hook and loop fastening systems may be utilized wherein the tab attachment structure 14 is comprised of a surface having either a hook or a loop material and at least a portion of the tabs 24 and 28, to be mated with said tab attachment structure 14, are comprised of the mating hook or loop material.

The configuration of the present ankle brace, shown in the figures, provides upper and lower sets of tabs generally dividing the ankle brace into an upper portion and a lower portion. The upper portion defines an interior having a first circumference. The lower portion defines an interior having a second circumference. The first and second circumference may be adjusted independently.

FIG. 1 shows a plurality of first tabs 24 each having at least one eyelet thereon. At least a portion of the tab 24 is constructed and arranged to releasably attach the tab 24 to a tab attachment structure 14.

Figure 2:
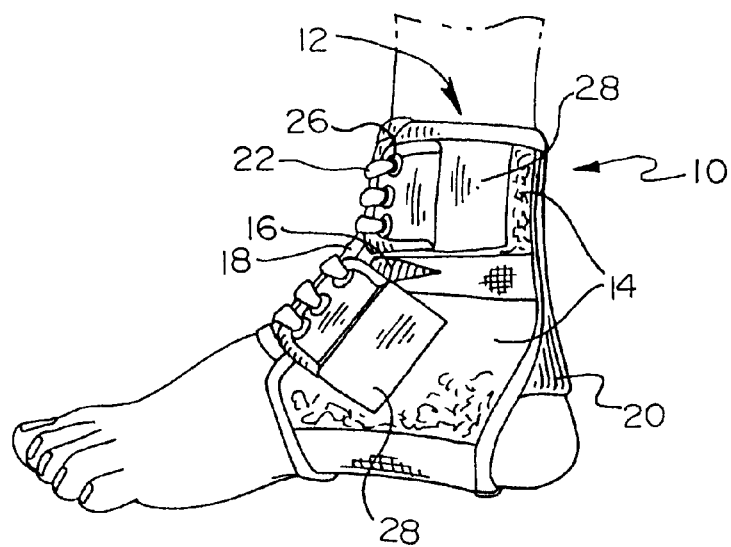
FIG. 2 is a side view of the second side of the embodiment of FIG. 1.
Figure 3:
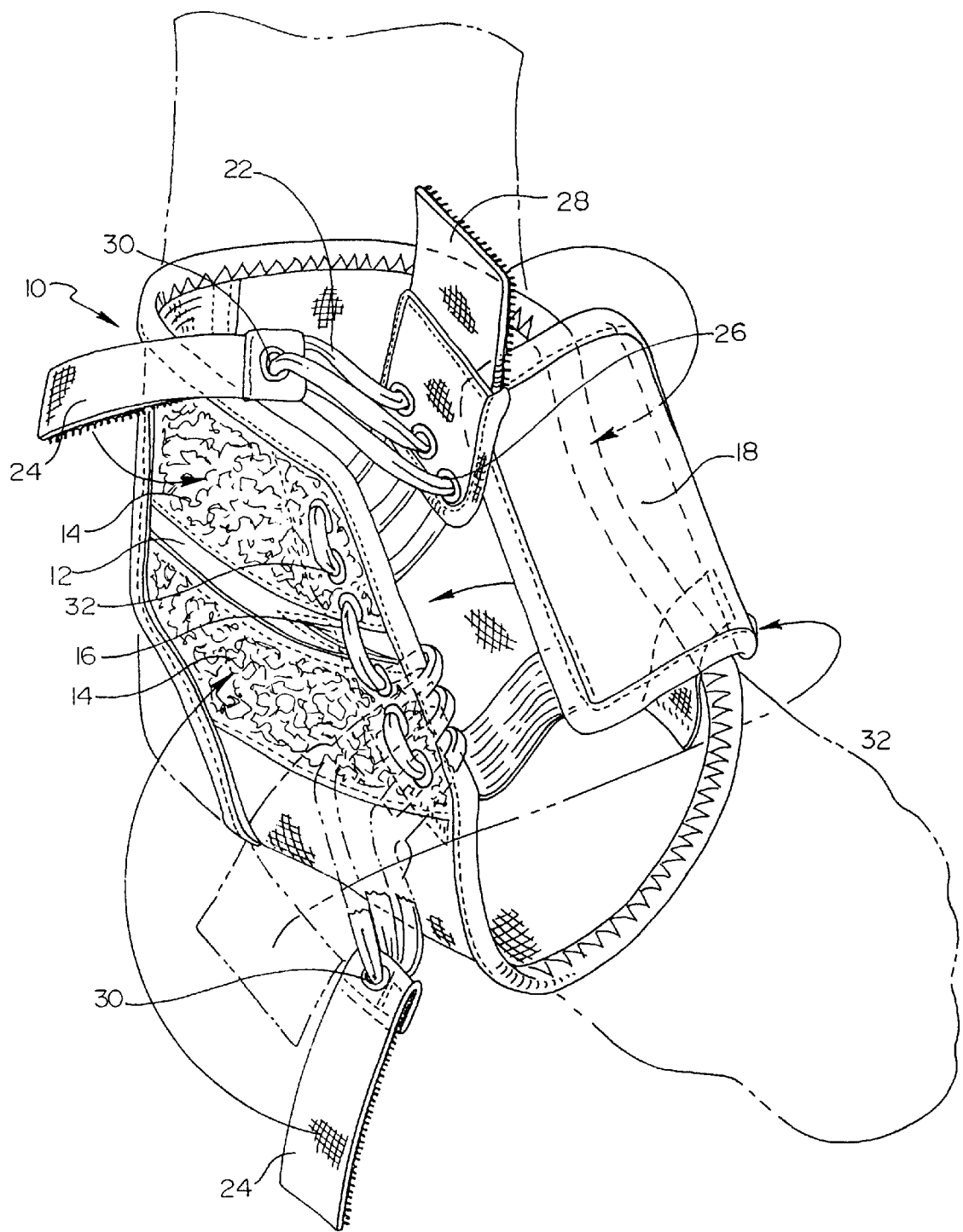
FIG. 3 is a front view of the embodiment of FIG. 1.

FIG. 2 shows a plurality of second tabs 28 having at least one eyelet 30 thereon. These tabs 28 also contain a portion that is constructed to releasably engage the tab 28 to a tab attachment structure 14. FIG. 2 also shows a plurality of eyelets 32, on the body 10 of the brace. The eyelets 32 are preferably aligned along the front edge of one of the side portions 12.

The plurality of eyelets on the first and second tabs 24 and 28 and the body 10 are utilized in conjunction with one or more laces and the eyelets 32 to adjust the size and tightness of the brace. The use of a plurality of tabs 24 and 28 allows the body 10 of the brace to be independently adjusted over two or more portions of the body 10. For example, the brace shown in FIGS. 1–4 utilizes two sets of tabs, an upper set controlling the upper portion of the body 10 and a lower set controlling the portion of the body 10. Each set of tabs is comprised of at least one first tab 24 and one second tab 28.

This structure provides an adjustment to the size of the circumference of the interior within the upper portion, by repositioning the tabs 24 and 28 attached to the upper tab attachment structure 14, while allowing the size of the circumference of the interior of the lower portion to be independently adjusted by movement of the lower set of tabs 24 and 28 attached to the lower tab attachment structure 14.

The number of eyelets on the body and the tabs may be any suitable number. One embodiment, as shown in FIGS. 1–4, provides a brace wherein the first tabs 24 have three eyelets 26, the second tabs 28 have one eyelet 30, and the body 10 has six eyelets 32. Any desired number of eyelets 32 on the body 10 and corresponding eyelets 26 may be employed within the scope of the present invention. It is contemplated that a single eyelet 30 is all that is required on the second tabs 28 to accomplish the purposes of the present invention.

When a lace is threaded through this configuration of eyelets, the brace not only provides independent upper and lower portion adjustment, but can additionally provide independent gross and fine adjustments for each set of tabs. Generally, in this embodiment, the first tabs 24 provide for gross adjustment of a portion of the brace, while the second tabs 28 provide for fine adjustment. The lacing and arrangement of the eyelets of this embodiment is shown in detail in FIG. 3.

The lacing of this embodiment is accomplished as follows. The tabs and eyelets are arranged having an upper set of tabs including one first tab 24 and one second tab 28 and a lower pair of tabs having one first tab 24 and one second tab 28. The lace 22 is threaded from one end that is attached to the second tab 28, through a first eyelet 26 on the first tab 24 of the upper pair of tabs, through a first and back through a second eyelet 32 on the body 10, through the second eyelet 26 on said first tab 24 of the upper pair of tabs, through a single eyelet 30 on the second tab 28 of the upper pair of tabs, through the third eyelet 26 on the first tab 24 of the upper pair of tabs, and through a third and back through a fourth eyelet 32 on the body 10. This lacing sequence provides the lacing of the upper portion of the brace.

The lacing continues on to the lower portion from the fourth eyelet 32, through a first eyelet 26 on the first tab 24 of the lower pair of tabs, through the single eyelet 30 on the second tab 28 of the lower pair of tabs, through a second eyelet 26 on the first tab 24 of the lower pair of tabs, through a fifth and back through a sixth eyelet 32 on the body 10, through a third eyelet 26 on the first tab 24 of the lower pair of tabs, and back to the second tab 28 of said lower pair of tabs, where the end of the lace 22 is attached thereto.

The arrangement of the lace 22 and the plurality of eyelets 26, 30, and 32 allows the user to first affix the first tabs 24 in place. Since the tabs have the laces threaded therethrough, the positioning and attachment of the first tabs 24 to the tab attachment structures 14 on the body 10 either loosens or tightens the lace 22 and thereby either enlarges or reduces the circumference of a portion of the body 10. This allows the user to roughly size the boot-shaped body 10 to fit the foot on which this device is placed and establishes a general size and tightness for each portion of the brace. The user can then utilize the second tabs 28, to make fine adjustments to each of the portions as desired, without disrupting the gross adjustments made with the first tabs 24. This is accomplished by the attachment of the second tabs 28 to the attachment structures 14. The pulling or slacking of the lace 22, attached or threaded through each tab 28, either loosens or tightens the lace 22 and, thereby, either further enlarges or reduces the circumference of that portion of the body 10.

Since many possible embodiments may be made of the present invention without departing from the scope thereof, it is to be understood that all matter herein set forth or shown in the accompanying drawings is to be interpreted in the illustrative and not limiting sense.

What is claimed is:

1. An ankle brace having an upper portion defining an interior having a first circumference and a lower portion defining an interior having a second circumference and first means for adjusting the size of the first circumference and a second means for adjusting the size of the second circumference, said first and second means being separated from each other and independently adjustable with respect to independently each other.

2. The ankle brace according to claim 1, wherein said first and second means for adjusting the size of the first and second circumferences comprises independent means for gross adjustment and fine adjustment.

3. An ankle brace according to claim 2, wherein said means for gross adjustment is provided by a set of tabs each having at least one lace receiving eyelet thereon and means for releasable attachment of each said tab to said body, one of said tabs being releasably attached to said upper portion of said brace and the other said tab being releasably attached to said lower portion.

4. An ankle brace according to claim 2, wherein said means for fine adjustment is provided by a set of tabs each having a lace receiving eyelet thereon and means for releasable attachment of each said tab to said body, one of said tabs being releasably attached to said upper portion of said brace and the other said tab being releasably attached to said lower portion.

5. An ankle brace according to claim 2, wherein said means for gross adjustment is provided by a set of first tabs each having at least one lace receiving eyelet thereon and means for releasable attachment of each said first tab to said body, one of said first tabs being releasably attached to said upper portion of said brace and the other first tab being releasably attached to said lower portion and wherein said means for fine adjustment is provided by a set of second tabs each having an eyelet thereon for receiving said lace and means for releasable attachment of each said second tab to said body, one of said second tabs being releasably attached to said upper portion of said brace and the other second tab being releasably attached to said lower portion.

6. An ankle brace according to claim 2, wherein said brace is comprised of a body, formed by the upper and lower portions, having an open front and being adapted to receive a lace, and wherein said means for adjustment of the size of the lower portion of said brace is provided by a set of tabs each having an eyelet thereon for receiving a lace and means for releasable attachment of each said tab to said body, one of said tabs being releasably attached to said body on one side of said front opening and the other tab being releasably attached to said body on the other side of said front opening and wherein said means for adjustment of the size of the upper portion of said brace is provided by a pair of tabs each having an eyelet thereon for receiving a lace and means for releasable attachment of each said tab to said body, one of said tabs being releasably attached to said body on one side of said front opening and the other tab being releasably attached to said body on the other side of said front opening.

7. The ankle brace according to claim 6, wherein each pair of tabs utilizes one tab for gross adjustment and one tab for fine adjustment of the portion of said brace to which the pair is releasably attached.

8. The ankle brace according to claim 1, wherein said brace is comprised of a body, formed by the upper and lower portions, having an open front and being adapted to receive a lace, said lace spanning said open front and received by said body, and said first and second means means for adjusting the size of the first and second circumferences being comprised of a plurality of tabs each having an eyelet for receiving said lace and constructed and arranged to be releasably and adjustably attached to said body, said tabs and lace being constructed and arranged to provide an independent means for both gross adjustment and fine adjustment of the sizes of the first and second circumferences.

9. An ankle brace, comprising:
a base comprising two side portions and a bottom portion, each said side portion having a front and a back edge, said back edges joined together and said side portions defining an interior having a circumference;
a plurality of tab attachment structures provided on each side portion;
a plurality of first tabs each having at least one eyelet thereon and constructed for releasable attachment to one of said tab attachment structures;
a plurality of second tabs each having an eyelet thereon and constructed for releasable attachment to one of said tab attachment structures an upper adjustment assembly comprising a first tab and a second tab;
a lower adjustment assembly comprising a first tab and a second tab; and
a lace constructed and arranged to be received within said eyelets and to be utilized with said first tabs to provide gross adjustment and with said second tabs to provide fine adjustment to the size of the circumference of said brace interior.

10. The ankle brace according to claim 9, further comprising a plurality of eyelets on one of said side portions.

11. The ankle brace according to claim 9, wherein said plurality of first tabs each have a plurality of eyelets thereon and constructed for releasable attachment to one of said tab attachment structures.

12. The ankle brace according to claim 9, wherein said plurality of second tabs each has a single eyelet thereon.

13. The ankle brace according to claim 9, wherein said lace has two ends each attached to a different one of said first or second tabs.

14. The ankle brace according to claim 9, wherein said brace has two tab attachment structures provided on each side portion, two first tabs, and two second tabs and wherein said lace has two ends each attached to a different one of said second tabs.

15. An ankle brace, comprising:
a generally U-shaped base comprising two side portions and a bottom portion, each said side portion having a front and a back edge with said side portions defining an interior having a circumference;
a plurality of eyelets on one of said side portions;
a plurality of tab attachment structures provided on each side portion;
a plurality of first tabs each having a plurality of eyelets thereon and constructed for releasable attachment to one of said tab attachment structures;
a plurality of second tabs each having a single eyelet thereon and constructed for releasable attachment to one of said tab attachment structures; and
a lace constructed and arranged to be received within said eyelets and to be utilized with said first tabs to provide gross adjustment and with said second tabs to provide fine adjustment to the size of the circumference of said brace interior.

16. The ankle brace according to claim 15, wherein said lace has two ends and each said end is attached to one of said first tabs and wherein said lace is threaded from one end, through said second tab, through said body and back to said first tab.

17. The ankle brace according to claim 15, wherein said lace has two ends and each said end is attached to one of said first or second tabs, wherein said brace has two tab attachment structures provided on each side portion, two first tabs each having a single eyelet, and two second tabs each having three eyelets thereon, wherein said side portion has six eyelets.

18. The ankle brace according to claim 17, wherein said tabs are arranged having an upper pair comprising one first tab and one second tab and a lower pair having one first tab and one second tab and wherein said lace is threaded from one end, through a first eyelet on said first tab of said upper pair, through a first and back through a second eyelet on said body, through said second eyelet on said first tab of said upper pair, through said single eyelet on said second tab of said upper pair, through said third eyelet on said first tab of said upper pair, through a third and back through a fourth eyelet on said body, through a first eyelet on said first tab of said lower pair, through the single eyelet on said second tab of said lower pair, through a second eyelet on said first tab of said lower pair, through a fifth and back through a sixth eyelet on said body, through a third eyelet on said first tab of said lower pair, and back to said first tab of said lower pair.

19. The ankle brace according to claim 15, wherein said side portions are joined by a back portion attached to and spanning between said side portions in proximity to said back edges.

20. The ankle brace according to claim 19, wherein said back portion is constructed from a material capable of stretching in multiple directions.

21. The ankle brace according to claim 15, wherein a notch is defined, in each said side portion, in proximity to the center of said front edges.

22. The ankle brace according to claim 21, wherein said notch has a material, capable of stretching in multiple directions, positioned therein.

* * * * *